United States Patent
Friedrich et al.

(10) Patent No.: US 10,392,332 B2
(45) Date of Patent: Aug. 27, 2019

(54) FLUORINATED TENSIDES

(71) Applicant: MERCK PATENT GmbH, Darmstadt (DE)

(72) Inventors: Reiner Friedrich, Seeheim-Jugenheim (DE); Gerhard Jonschker, Heppenheim (DE)

(73) Assignee: MERCK PATENT GmbH, Darmstadt (DE)

( * ) Notice: Subject to any disclaimer, the term of this patent is extended or adjusted under 35 U.S.C. 154(b) by 189 days.

(21) Appl. No.: 15/500,368

(22) PCT Filed: Jul. 15, 2015

(86) PCT No.: PCT/EP2015/001449
§ 371 (c)(1),
(2) Date: Jan. 30, 2017

(87) PCT Pub. No.: WO2016/015830
PCT Pub. Date: Feb. 4, 2016

(65) Prior Publication Data
US 2017/0217863 A1  Aug. 3, 2017

(30) Foreign Application Priority Data

Jul. 28, 2014  (EP) ..................................... 14002621

(51) Int. Cl.
| | | |
|---|---|---|
| *C09D 7/45* | (2018.01) |
| *C11D 1/00* | (2006.01) |
| *C07C 41/03* | (2006.01) |
| *C07C 41/06* | (2006.01) |
| *C07C 43/17* | (2006.01) |
| *C07C 217/28* | (2006.01) |
| *C07C 217/40* | (2006.01) |
| *C07C 43/13* | (2006.01) |
| *C07C 41/16* | (2006.01) |
| *C07C 41/26* | (2006.01) |
| *C07C 213/02* | (2006.01) |
| *C09J 11/06* | (2006.01) |

(52) U.S. Cl.
CPC ............ *C07C 43/137* (2013.01); *C07C 41/03* (2013.01); *C07C 41/06* (2013.01); *C07C 41/16* (2013.01); *C07C 41/26* (2013.01); *C07C 43/17* (2013.01); *C07C 213/02* (2013.01); *C07C 217/28* (2013.01); *C07C 217/40* (2013.01); *C09D 7/45* (2018.01); *C09J 11/06* (2013.01); *C11D 1/004* (2013.01)

(58) Field of Classification Search
CPC .......... C07C 43/12–126; C07C 43/137; C08G 65/226; C08G 65/2639
See application file for complete search history.

(56) References Cited

U.S. PATENT DOCUMENTS

| | | |
|---|---|---|
| 4,968,599 A | 11/1990 | Pitt et al. |
| 4,988,610 A | 1/1991 | Pitt et al. |
| 5,157,159 A | 10/1992 | Janulis et al. |
| 5,567,857 A | 10/1996 | Huang et al. |
| 6,340,779 B1 | 1/2002 | Enna et al. |
| 6,706,923 B2 | 3/2004 | Haniff et al. |
| 6,890,608 B2 | 5/2005 | Morishima et al. |
| 7,635,789 B2 | 12/2009 | Foo et al. |
| 7,737,307 B2 | 6/2010 | Murphy et al. |
| 8,008,358 B2 | 8/2011 | Kirsch et al. |
| 8,058,480 B2 | 11/2011 | Moloy |
| 8,263,800 B2 | 9/2012 | Murphy et al. |
| 9,115,062 B2 | 8/2015 | Hierse et al. |
| 2003/0153780 A1 | 8/2003 | Haniff et al. |
| 2008/0093582 A1 | 4/2008 | Nagai et al. |
| 2008/0149878 A1 | 6/2008 | Kirsch et al. |
| 2008/0234389 A1* | 9/2008 | Mecozzi ............. A61K 9/0019 514/722 |
| 2009/0043133 A1 | 2/2009 | Murphy et al. |
| 2010/0003737 A1 | 1/2010 | Murphy et al. |
| 2011/0088594 A1 | 4/2011 | Claus et al. |
| 2011/0118428 A1 | 5/2011 | Hierse et al. |
| 2012/0111233 A1 | 5/2012 | Hierse et al. |
| 2013/0269568 A1 | 10/2013 | Claus et al. |

FOREIGN PATENT DOCUMENTS

| | | |
|---|---|---|
| JP | H09111286 A | 4/1997 |
| JP | 2001133984 A | 5/2001 |
| JP | 2004264830 A | 9/2004 |
| JP | 2014037362 A * | 2/2014 |
| RU | 2559319 C1 | 8/2015 |
| WO | 9535272 A1 | 12/1995 |
| WO | 03010128 A2 | 2/2003 |
| WO | 2006072401 A1 | 7/2006 |
| WO | 2009020907 A1 | 2/2009 |
| WO | 2009149807 A1 | 12/2009 |

(Continued)

OTHER PUBLICATIONS

Parlato, M. C. et al. Synthesis, characterization, and applications of hemifluorinated dibranched amphiphiles. Journal of Organic Chemistry, 2011, 76, 6584-6591. (Year: 2011).*
Machine Translation of JP2014-037362A. Feb. 27, 2014 (Year: 2014).*
International Search Report for PCT/EP2015/001449 dated Sep. 22, 2015.
Scheibe, P. et al., "Langmuir-Blodgett Films of Fluorinated Glycolipids and Polymerizable Lipids and Their Phase Separating Behavior," Langmuir, Dec. 7, 2010, vol. 26, No. 23, pp. 18246-18255.

(Continued)

*Primary Examiner* — Stephen E Rieth
(74) *Attorney, Agent, or Firm* — Millen White Zelano & Branigan, PC

(57) ABSTRACT

The present invention relates to novel compounds containing fluorinated end groups, to the use thereof as surface-active substances, and to compositions comprising these compounds.

15 Claims, 1 Drawing Sheet

(56) References Cited

FOREIGN PATENT DOCUMENTS

| WO | 2010002623 A2 | 1/2010 |
|---|---|---|
| WO | 2010003567 A2 | 1/2010 |
| WO | 2010149262 A1 | 12/2010 |
| WO | 2011082770 A2 | 7/2011 |
| WO | 2012084118 A1 | 6/2012 |

OTHER PUBLICATIONS

Tucker, W. B. et al., "Synthesis, physicochemical characterization, and self-assembly of linear, dibranched, and miktoarm semifluorinated triphilic polymers," Journal of Polymer Science Part A: Polymer Chemistry, Dec. 1, 2014, vol. 52, No. 23, pp. 3334-3336.
English Abstract of JP200133984, Publication Date: May 18, 2001.
English Abstract of WO2011082770, Publication Date: Jul. 14, 2011.
Goto, Kotaro et al., "Preparation of odorless thiol derivatives with an aglycon rearrangement inhibitory effect," Database CA Online Chemical Abstracts Service, Feb. 27, 2014.
Broll, K. et al., "Funktionsweise von Tensiden," Mar. 31, 2014.
Malfait, Stephane et al., "Synthesis of bi- and tetracatenar highly fluorinated compounds for grafting on silicone materials," Database CA Online Chemical Abstracts Service, 2011.
Tamiaki, Hitoshi et al., "Self-aggregation of zinc chlorophylls possessing perfluoroalkyl chains in fluorous solvents: Selective extraction of the self-aggregates with fluorous phase and accelerated formation of the ordered supramolecules in this phase," Database CA Online Chemical Abstracts Service, 2007.
Huang, Wenjian et al., "Synthesis of ether-linked fluorocarbon surfactants and their aggregational properties in organic solvents," Database CA Online Chemical Abstracts Service, 2004.
Ariga, Katsuhiko et al., "A QCM study on adsorption of macrocyclic sugar-cluster to variously-functionalized monolayers," Database CA Online Chemical Abstracts Service, 1998.
Liu, Zhao-Tie et al., "Phase behaviors of Aerosol-OT Analogue Fluorinated Surfactants in 1,1,1,2-Tetrafluoroethane and Supercritical CO2," Ind. Eng. Chem. Res., 2007, vol. 46, No. 1, pp. 22-28.
Pitt, A. R., "The efficiency of dynamic surface tension reductions within homologous series of surfactants in aqueous gelatin solution," Progr Colloid Polym Sci, 1997, vol. 103, pp. 307-317.
Pitt, A. R. et al., "The relationship between surfactant structure and limiting values of surface tensions, in aqueous gelatin solution, with particular regard to multilayer coating," Colloids and Surfaces A: Physicochemical and Engineering Aspects, 1996, vol. 114 pp. 321-335.
Carolina Dos Ramos, M. et al., "Theoretical investigation of the phase behaviour of mixtures of a novel family of perfluoroalkyl-polyoxyethylene ether diblock surfactants in aqueous solutions of carbon dioxide," The Journal of Supercritical Fluids, 2010, vol. 55, pp. 802-816.
Heilmann, S. M. et al., "O-hydroxyethylation of 1,1-dihydroperfluorinated alcohols," Journal of Fluorine Chemistry, 1992, vol. 59, pp. 387-396.
English Abstract for JP2004264830, Publication Date: Sep. 24, 2004.
Adkins S S etal: "Effect of branching on the interfacial properties of nonionic hydrocarbon surfactants at the airwater and carbon dioxidewater interfaces", Journal of Colloid and Interface Science, Academic Press,Inc, US,vol. 346, Nr. 2, (Jun. 15, 2010), pp. 455-463, XP027030384, ISSN: 0021-9797.
Office Action in corresponding EP application No. 15738275.5 dated Oct. 1, 2018 (pp. 1-4).
Office Action in corresponding RU application No. 2017-106261 dated Feb. 11, 2019 (pp. 1-2).

* cited by examiner

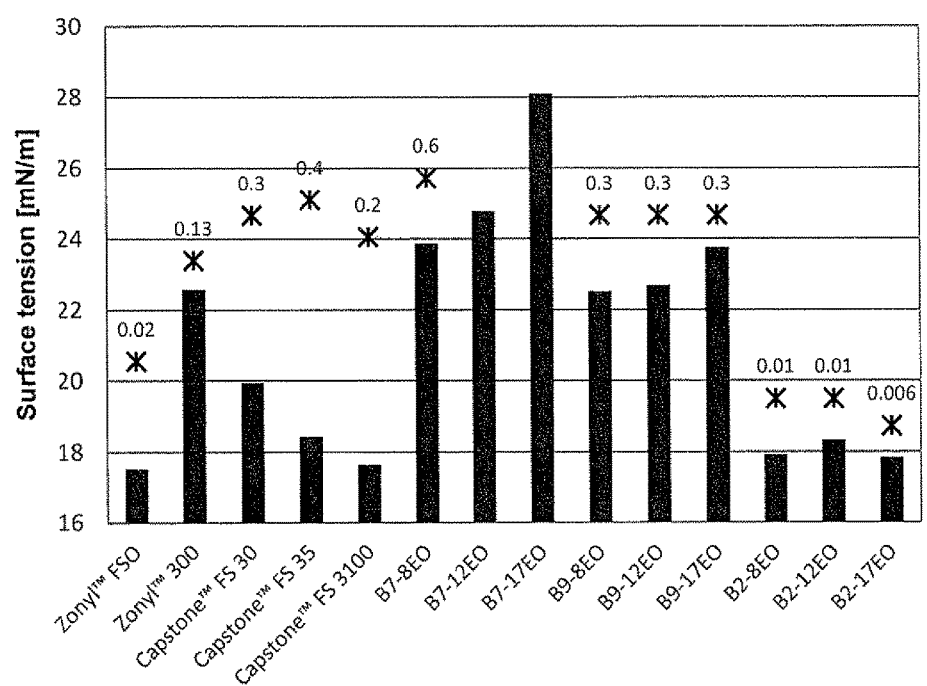

FLUORINATED TENSIDES

The present invention relates to novel compounds containing fluorinated end groups, to the use thereof as surface-active substances, and to compositions comprising these compounds.

Fluorosurfactants are employed in various applications and contribute, for example, to improved wetting of surfaces. Thus, they are used, for example, as interface promoters or emulsifiers or viscosity reducers in paints, coatings or adhesives.

Fluorine-containing, non-ionic surfactants are usually based on fluorinated alkyl chains and hydrophilic polyethylene glycol units. Owing to the chain length of 6 to 8 carbon atoms of the perfluorinated part, surfactants of this type are potentially bioaccumulative, persistent and toxic. Shorter perfluorinated alkyl chains having 2-5 carbon atoms are known to be less toxic and bioaccumulative, but exhibit inadequate efficacy.

JP-A-2001/133984 discloses surface-active compounds containing perfluoroalkoxy chains which are suitable for use in antireflection coatings. JP-A-09/111286 discloses the use of perfluoropolyether surfactants in emulsions. WO 2006/072401 and WO 2010/003567 describe surface-active compounds containing trifluoromethoxy groups. Compounds containing specific fluoroalkyl groups are described in U.S. Pat. Nos. 7,635,789, 7,737,307, US 2008/0093582, JP 2004-18394 and WO 2010/002623. In addition, the compound $CF_3$—$CF_2$—$CF_2$—O—$CH_2$—$CH_2$—OH is known (CAS 1313023-37-8), and theoretical investigations on mixtures of $CO_2$ and perfluoroalkyl surfactants in aqueous solutions are described in J. of Supercritical Fluids 55 (2010) 802-816. WO 03/010128 describes perfluoroalkyl-substituted amines, acids, amino acids and thioether acids which contain a $C_{3-20}$-perfluoroalkyl group. Specific applications of sulfosuccinates and/or sulfotricarballylates containing various fluorinated side chains are described in U.S. Pat. Nos. 4,968,599 and 4,988,610 and 6,890,608 and in A. R. Pitt et al., Colloids and Surfaces A: Physicochemical and Engineering Aspects, 1996, 114, 321-335; A. R. Pitt, Progr. Colloid Polym. Sci, 1997, 103, 307-317 and Z.-T. Liu et al., Ind. Eng. Chem. Res. 2007, 46, 22-28. Further fluorosurfactants, in particular succinates and tricarballylates containing fluorinated alkyl groups, are described in WO 2009/149807, WO 2010/003567, WO 2010/149262, WO 2011/082770 and WO 2012/084118.

There continues to be a demand for alternative surface-active substances which preferably do not degrade to form long-chain persistent compounds or are preferably equally effective as conventional fluorosurfactants in lower dosage.

Novel compounds which are suitable as surface-active substances have now been found.

The present invention relates firstly to compounds of the formula (I),

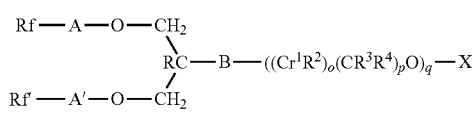

(I)

where
R is equal to H, alkyl, —OH or —$CH_2$—O-$A'''_{a'''}$—$Rf''$,
Rf, Rf' and Rf'' are, independently of one another, equal to $CF_3$—$CF_2$—$CF_2$—O—$CF(CF_3)$—$CH_2$— or $CF_3$—$(CF_2)_n$—$(CH_2)_m$—, where n=1-7 and m=1-10,
$R^1$-$R^4$ are, independently of one another, equal to hydrogen or a C1-C4 alkyl group, o and p are, independently of one another, 0-4, o+p≥2 and q≥1,
A, A' and A'' are, independently of one another, equal to (O—$(CR^5R^6)_r$—$(CR^7R^8)_s$)$_t$,
where $R^5$-$R^8$ are, independently of one another, equal to hydrogen or a C1-C4 alkyl group, r and s are, independently of one another, 0-4 and t=0 or 1,
B is $(CH_2)_{0-1}$—O or $(CH_2)_{0-1}$—NR',
where R'=H or linear or branched alkyl,
and
X is equal to H or linear or branched alkyl.

Preference is given to compounds of the formula (I) which include one or more of the following preferred variables:

n is preferably 1-5.
m is preferably 1-3.
R is preferably equal to H or OH.
B is preferably equal to O, $CH_2$—O or $CH_2$—NR', where R' is preferably equal to H or $CH_3$, in particular H.
o and/or p are preferably equal to 1-4, in particular 1-2.
q is preferably 1-100, in particular 1-40, particularly preferably 1-20, especially 5-18.

In a variant of the invention, t is preferably equal to 0.

The group $((CR^1R^2)_o$—$(CR^3R^4)_pO)_q$ preferably encompasses one or more of the groups $(CH_2CH_2O)_q$, $(CH_2CH_2CH_2CH_2O)_q$ and/or $(CHR^2CHR^4O)_q$, where one of the groups $R^2$ and $R^4$ is equal to $CH_3$ or $C_2H_5$ and the other group $R^2$ or $R^4$ is equal to H, and q=1-40, preferably 1-20, in particular 5-18. The group $((CR^1R^2)_o$—$(CR^3R^4)_pO)_q$ preferably encompasses polyethylene glycol, polypropylene glycol, polyisobutylene glycol and/or polybutylene glycol units.

A, A' and A'' can preferably also be equal to —O—$CH_2$—$CHR''$—, where R'' is equal to H or $CH_3$.

X is preferably equal to H or $CH_3$.

Preferably, Rf, Rf' and Rf'' are identical and/or A, A' and A'' are identical.

Compounds of the formula (I) in which one or more of the variables have the preferred meanings are particularly advantageous. Compounds of the formula (I) in which all said variables simultaneously have the preferred meanings, in particular the particularly preferred meanings, are particularly advantageous. Compounds according to claims 2 and 3 are particularly preferred here.

Preference is given to compounds of the formula (I) in which:

Rf and Rf' are $CF_3$—$CF_2$—$CF_2$—O—$CF(CF_3)$—$CH_2$—, $C_2F_5$—$CH_2$— or $C_3F_7$—$CH_2$—,
R is equal to H or OH,
B is equal to O or $CH_2$—NR', where R' is equal to H or $CH_3$,
the group $((CR^1R^2)_o$—$(CR^3R^4)_pO)_q$ is equal to a polyethylene glycol or polypropylene glycol unit,
q is equal to 1-40, preferably equal to 1-20, in particular 5-18,
t is equal to 0,
and X is equal to H.

Rf and Rf' here are particularly preferably identical.

Preferred compounds of the invention are reproduced in the formula (I'), in which the variables have the meanings described for formula (I):

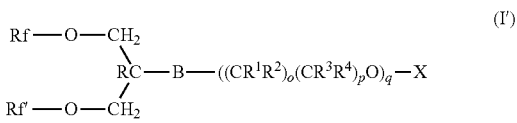
(I')

Particular preference is given to compounds of the formula (I') in which one or more of the variables have the preferred meanings described for formula (I). Compounds of the formula (I') in which all said variables simultaneously have the preferred meanings, in particular the particularly preferred meanings, described for formula (I) are particularly advantageous.

Particular preference is given to compounds of the formula (I') in which R=H or —OH, B=O, $CH_2$—O or $CH_2$—NR', where R'=H, $CH_3$ or $C_2H_5$, X=H or alkyl, preferably $CH_3$ or $C_2H_5$, and the group $((CR^1R^2)_o$—$(CR^3R^4)_pO)_q$, where q=1-40, preferably 1-20, in particular 5-18, is a polyethylene glycol, polypropylene glycol, polyisobutylene glycol and/or polybutylene glycol unit, preferably a polyethylene glycol or polypropylene glycol unit.

Preferred compounds are those of the formulae (II), (IIIa)/(IIIb) and (IVa)/(IVb), in particular (IVa):

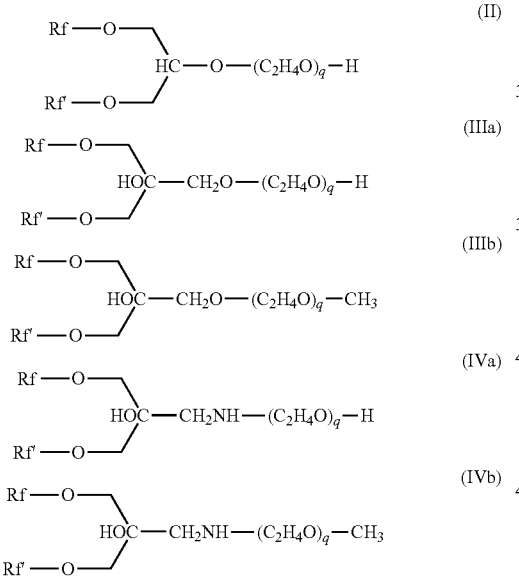

Especial preference is given to compounds of the formulae (II), (IIIa)/(IIIb) and (IVa)/(IVb), in particular (IVa), in which one or more of the variables have the preferred meanings described for formula (I) or (I'). Particularly preferred compounds according to the invention are compounds of the formulae (II), (IIIa), (IIIb), (IVa) and (IVb) in which Rf and Rf' are identical and q is equal to 1-40, preferably equal to 1-20, in particular 5-18.

The novel compounds preferably conform to the formulae (IIa), (IIb), (IIc), (IId), (IIIa-1) and (IVa-1):

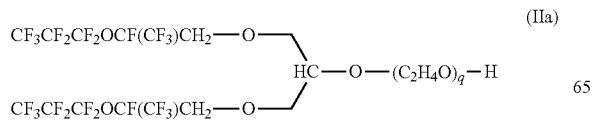

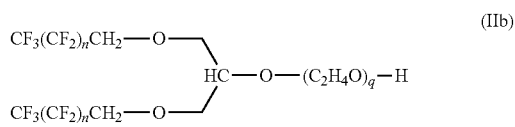
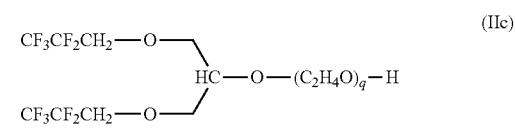
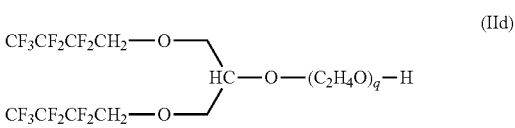
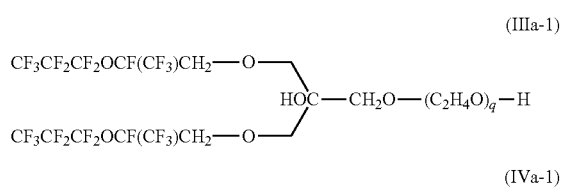

where n=1-4, in particular 1-2 (formulae (IIc) and (IId)), and in each case q=1-40, in particular 1-20, especially 5-18.

The compounds of the formula (I) according to the invention can be prepared by simple, standard process steps and starting from commercial starting materials, for example via the intermediates of the formula (VI) or (VII):

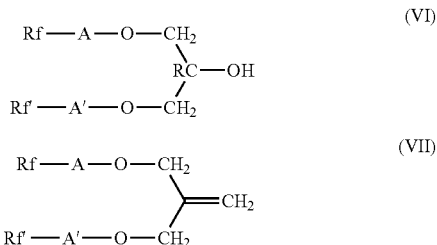

The preparation for the compounds of the formula (I') where Rf'=Rf, R=H or —OH, B=O, $CH_2$—O or $CH_2$—NH, the group $((CR^1R^2)_o$—$(CR^3R^4)_qO)_q$=polyethylene and X=H is shown by way of example below.

These compounds can preferably be prepared by a multistep synthesis starting from the corresponding alcohols of the formulae (Va) and (Vb):

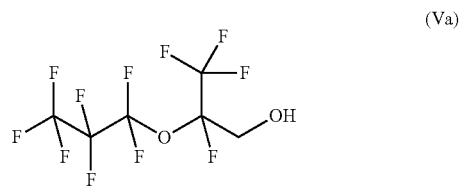

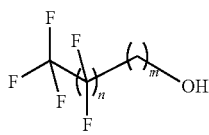

(Vb)

where n=1-7, preferably 1-5, and m=1-10, preferably 1-3.

These alcohols can be converted into the branched structures of the formula (VI'), where R is preferably equal to H or alkyl, in particular H, by reaction with 1,3-dichloropropan-2-ol or epichlorohydrin, where Rf is equal to the corresponding fluorine-containing groups of the formula (Va) or (Vb):

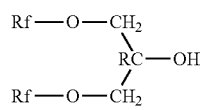

(VI')

The compounds of the formula (VI') can then be converted into the corresponding non-ionic surfactants of the formula (II') by alkylene oxide polymerisation, for example ethylene oxide or propylene oxide polymerisation. The performance of the said processes is familiar to the person skilled in the art (U.S. Pat. Nos. 5,567,857; 6,340,779; 8,058,480).

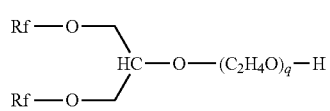

(II')

The alcohols of the formulae (Va) and (Vb) can also be converted into the branched structures of the formula (VII') by reaction with 3-chloro-2-chloromethyl-1-propene, where Rf is equal to the corresponding fluorine-containing groups of the formula (Va) or (Vb):

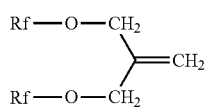

(VII')

The compounds of the formula (VII') can then be converted into the corresponding non-ionic surfactants, for example those of the formulae (IIIa')/(IIIb') or (IVa')/(IVb'), via the epoxide as intermediate by reaction with polyethylene glycols or aminopolyethylene glycols or the corresponding monoethers:

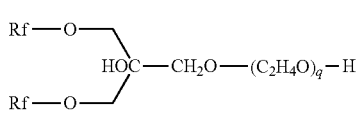

(IIIa')

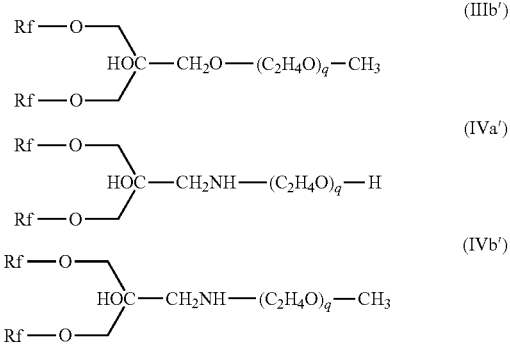

The performance of the said processes is familiar to the person skilled in the art. Conventional process parameters are shown by way of example in the experimental part. The preparation of further compounds of the formula (I), in particular of the formula (I'), according to the invention can be carried out analogously to the illustrative reactions shown. However, the preparation of further compounds of the formula (I) or (I') according to the invention can also be carried out by other methods known per se to the person skilled in the art from the literature.

The invention furthermore also relates to the compounds of the formulae (VI) and (VII) or of the formulae (VI') and (VII'), which can be prepared as described, where the variables have the meanings, in particular the preferred meanings, described for formula (I). The invention preferably relates to the compounds of the formulae (VI') and (VII'):

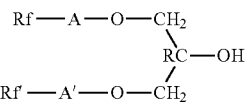

(VI)

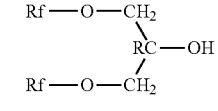

(VI')

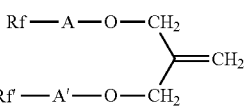

(VII)

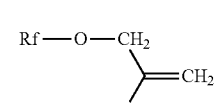

(VII')

The alcohols used are commercially available and/or their preparation starting from commercially available starting materials is familiar to the person skilled in the art (Heilmann et al. J. Fluorine Chem. 1992, 59, 387; Janulis et al. U.S. Pat. No. 5,157,159) or they can be prepared analogously to known synthetic processes, for example by reduction of methyl perfluoro(2-methyl-3-oxahexanoate (for example using LiAlH$_4$) and optionally chain extension using, for example, ethylene carbonate or propylene carbonate under conditions known to the person skilled in the art (U.S. Pat. No. 5,157,159).

The novel compounds may have low environmental toxicity and at the same time good surface activity.

Advantages of the compounds according to the invention may be, in particular:
- a surface activity which is equal or superior to that of conventional hydrocarbon surfactants with respect to efficiency and/or effectiveness,
- biological and/or abiotic degradability of the substances without formation of persistent perfluorinated degradation products, such as PFOA (perfluorooctanoic acid) or PFOS (perfluorooctanesulfonate),
- weak foaming action and/or low foam stabilisation,
- good processability in formulations and/or
- storage stability.

The compounds according to the invention preferably have a particular surface activity. The compounds of the formula (I) according to the invention, preferably of the formula (I'), in particular the compounds of the formula (II), (III) and (IV), may have significantly improved environmental properties compared with the fluorosurfactants of the prior art since they do not degrade either chemically or biologically to form long-chain PFCAs or PFASs.

The present invention furthermore relates to the use of the compounds according to the invention and the preferred embodiments described above as surface-active agents, for example for improving the flow behaviour and wetting capacity of coating formulations. Preference is given to the use of fluorosurfactants of the formula (I'), in particular of the formulae (II), (III) and (IV), in particular the particularly preferred compounds mentioned.

Besides the compounds of the formula (I), the mixtures according to the invention may also comprise solvents, additives, assistants and fillers as well as non-fluorinated surfactants. Mention may be made by way of example of silicone particles, plasticisers and surface-modified pigments.

Preferred areas of use are, for example, the use of the fluorosurfactants according to the invention as additives in preparations for surface coating, such as paints, lacquers, protective coatings, special coatings in electronic or semiconductor applications (for example photoresists, top antireflective coatings, bottom antireflective coatings) or in optical applications (for example photographic coatings, coatings of optical elements), in agrochemicals, in polishes and waxes, for example for furniture, floorcoverings and automobiles, in particular in floor polishes, in fire-extinguishing compositions, lubricants, or in photolithographic processes, in particular in immersion photolithography processes, for example in developer solutions, rinse solutions, immersion oils and/or in the photoresists themselves, especially for the production of printed circuits or in additive preparations for corresponding preparations.

In addition, the compounds which can be used in accordance with the invention as surfactant are suitable for washing and cleaning applications, and for use as additives/surfactants in cosmetic products, such as, for example, hair and bodycare products (for example shampoos, hair rinses and hair conditioners), foam baths, creams or lotions having one or more of the following functions: emulsifiers, wetting agents, foaming agents, lubricants, antistatic, enhancers of resistance to skin oils.

The compounds according to the invention can furthermore be used as additives in herbicides, pesticides and fungicides, with one or more of the following functions: substrate wetting agent, adjuvant, foam inhibitor, dispersant, emulsion stabiliser. In addition, the compounds according to the invention can also be used as additives in de-icing agents or icing preventers.

For use, the fluorosurfactants according to the invention are usually introduced into correspondingly designed preparations. Usual use concentrations are 0.01-1.0% by weight of the surfactants according to the invention, based of the entire preparation. The present invention likewise relates to corresponding compositions comprising the fluorosurfactants according to the invention. Such compositions preferably comprise a vehicle which is suitable for the respective application, and optionally further active substances and/or optionally assistants. Preferred compositions are paint and coating preparations, fire-extinguishing agents, lubricants, washing agents and detergents and de-icers or developer solutions, rinse solutions, immersion oils and photoresists for photolithographic processes, in particular for immersion photolithography processes and in particular for the production of printed circuits, agrochemicals, floor polishes, cosmetic products, cosmetic products or hydrophobicisation agents for textile finishing or glass treatment. Preferred compositions here are paint and coating preparations and printing inks.

In addition, the present invention also relates to water-based surface-coating formulations which comprise the fluorosurfactants according to the invention, alone or mixed with additives. Preference is given to the use of surface-coating formulations based on the following synthetic film formers: polycondensation resins, such as alkyd resins, saturated/unsaturated polyesters, polyamides/imides, silicone resins; phenolic resins; urea resins and melamine resins, polyaddition resins, such as polyurethanes and epoxy resins, polymerisation resins, such as polyolefins, polyvinyl compounds and polyacrylates.

In addition, the fluorosurfactants according to the invention are also suitable for use in surface coatings based on natural products and modified natural products. Preference is given to surface coatings based on oils, polysaccharides, such as starch and cellulose, and also based on natural resins, such as cyclic oligoterpenes, polyterpenes and/or shellac.

The fluorosurfactants according to the invention can be used both in physically hardening (thermoplastics) and in crosslinking (elastomers and thermosets) aqueous surface-coating systems. The fluorosurfactants according to the invention preferably improve the flow and wetting properties of the surface-coating systems.

The present invention relates to all uses mentioned here of fluorosurfactants to be employed in accordance with the invention. The respective use of fluorosurfactants for the said purposes is known to the person skilled in the art, and consequently the use of the fluorosurfactants to be employed in accordance with the invention presents no problems.

The complete disclosure contents of all applications and publications mentioned expressly also belong to the disclosure content of the present application by way of reference. Further features, advantages and variants of the invention also arise from the claims and examples. The following examples explain the present invention in greater detail without restricting the scope of protection.

EXAMPLES

Abbreviations $Et_2O$ diethyl ether
EtOAc ethyl acetate
MTBE tert-butyl methyl ether
HFPO alcohol 1H,1H-perfluoro(2-methyl-3-oxahexan-1-ol)

RT room temperature
DBTL dibutyltin dilaurate

Example 1

Synthesis of 1H,1H-perfluoro(2-methyl-3-oxahexan-1-ol) (CAS 2101-3-71)

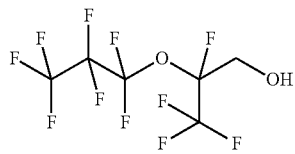

30 ml of absol. $Et_2O$ are initially introduced in a dry 500 ml four-necked flask with metal condenser, $CaCl_2$ drying tube, dropping funnel and thermometer, and 70 ml of 1M $LiAlH_4$ solution (0.07 mol) in $Et_2O$ are introduced via a septum. 44.30 g (0.12 mol) of methyl perfluoro(2-methyl-3-oxahexanoate) (ABCR, Karlsruhe Germany) in 50 ml of abs. $Et_2O$ are introduced into the dropping funnel.

The ester is added dropwise with stirring at such a rate that the exothermicity of the reaction maintains the diethyl ether at the boil. When the addition is complete, the reaction mixture is stirred under reflux for a further 1.5 hours. A cloudy dispersion forms in the course of the reaction. The batch is cooled in an ice bath. The excess $LiAlH_4$ is decomposed by addition of 10 ml of EtOAc with slight evolution of heat. 10 g of $H_2O$ are subsequently added, after which a flocculent aluminium hydroxide precipitate forms. 78 g of 25% sulfuric acid is added dropwise to the suspension over the course of 30 minutes, during which a clear two-phase mixture forms. The organic phase is separated off, and the aqueous phase is washed with 3×40 ml of $Et_2O$. The organic phases are combined, washed with 3×40 ml of $H_2O$ and dried over $Na_2SO_4$. The ether is distilled off, and the residue is subjected to fractional distillation. Product: 31.8 g (b.p. 57° C./100 mbar); purity 91% (GC-MS); yield 73% of theory

Example 2

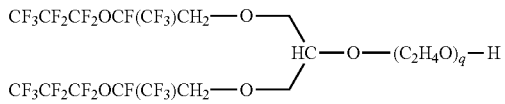

37.9 g of the HFPO alcohol from Example 1 and 5.0 g of 1,3-dichloropropan-2-ol are initially introduced in a 250 ml 3-necked flask. 6.52 g of powdered KOH are added with ice-cooling. During this addition, the temperature is kept below 10° C. When the addition is complete, the batch is warmed to 110° C. and stirred at this temperature for 16 hours.

The mixture is subsequently cooled to RT, and 50 ml of water are added. The organic phase is separated off, and the aqueous phase is extracted again with 3×50 ml of dichloromethane. The combined organic phases are then washed with 50 ml of water and dried over sodium sulfate.

After the solvent has been distilled off, the material is distilled in vacuo. B.p. 80-83° C./0.1 mbar; yield 17.56 g.

The branched alcohol is reacted with ethylene oxide in a pressure reactor in accordance with the prior art. (Conditions: 140° C.; maximum pressure 4 bar). The reaction is terminated when the polyethylene oxide chain statistically contains 8, 12 and 17 units. The static surface tension of the compounds and the critical micelle concentration (CMC) are reproduced in FIG. 1 as measurement values B2-8EO, B2-12EO and B2-17EO.

Example 3

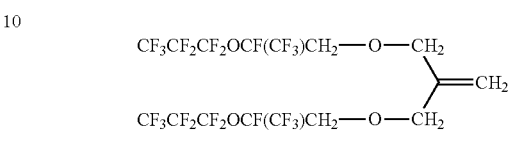

17.5 g of HFPO alcohol and 3 ml of 3-chloro-2-chloromethyl-1-propene are initially introduced in 30 ml of toluene. Powdered KOH is added with ice-cooling (temp. 0-10° C.). The mixture is subsequently heated to 110° C. and stirred at this temperature for 65 h. 50 ml of water are added to the batch, which is then extracted 3 times with 25 ml of MTBE. The combined organic phases are washed with 25 ml of water and dried over sodium sulfate. The batch is distilled in vacuo. B.p. 110-118° C./5 mbar; yield: 10 g.

Example 4

Epoxidation 6 g of 3-chloroperoxybenzoic acid are dissolved in 25 ml of dichloromethane at room temperature and subsequently cooled to 10° C. 7 g of product from Example 3 are dissolved in 5 ml of dichloromethane and added to the batch, and the mixture is stirred at room temperature for 24 hours. The batch is filtered, and the filtrate is washed by shaking with 50 ml of 10% $NaHSO_3$. The organic phase is separated off, dried and evaporated. Yield 5.59 g.

Example 5

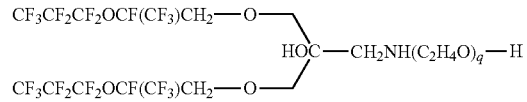

5 g of material from Example 4 are combined with 4 g of aminopolyethylene glycol (MW 560) and one drop of DBTL and warmed to 120° C. After 5 hours, the batch is a single phase. The batch is cooled to RT and passed through a short silica-gel column (10 g) with dichloromethane until the filtrate is colourless. The product is subsequently washed from the column using ethanol, the solvent is distilled off, and the residue is dried in vacuo (pale-yellow oil, yield: 8 g).

The static surface tension is $\gamma=20.3$ mN/m (0.1 g/l of $H_2O$).

Example 6

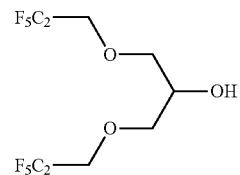

265.5 g of pentafluoropropanol and 217 g of DI water are initially introduced in a reactor with internal thermometer and reflux condenser and heated to a temperature of 30° C. 74.8 g of epichlorohydrin are added with stirring, and 56.11 g of a 47% KOH solution are subsequently slowly added dropwise. The metering rate here is selected so that the temperature of the reaction solution does not rise above 32° C. Towards the end of the addition, the batch becomes noticeably cloudy, with the viscosity increasing. When the addition is complete, the mixture is stirred at 70° C. for a further 15 h. The batch is cooled to room temperature, adjusted to pH 7 using dil. HCl, the organic phase is separated off and distilled in vacuo: yield 83%, 285 g. Purity 98% (GC).

Example 7

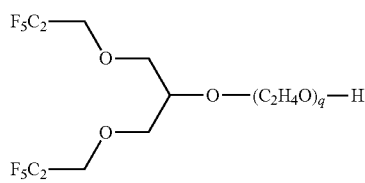

The alcohol prepared in Example 6 is reacted with ethylene oxide in a pressure reactor at 140° C. and a maximum pressure of 4 bar to give the corresponding fluorosurfactant. Different chain lengths can be achieved corresponding to the reaction time. Three materials having a statistically distributed recurring unit of 8, 12 and 17 are obtained. The material is freed from low-boiling impurities by vacuum distillation. The static surface tension of the compounds and the CMC are reproduced in FIG. 1 as measurement values B7-8EO, B7-12EO and B7-17EO.

Example 8

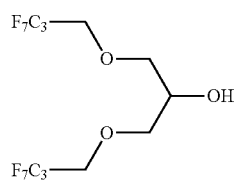

180.7 g of heptafluorobutanol and 230 g of DI water are initially introduced in a reactor with internal thermometer and reflux condenser and heated to a temperature of 30° C. 40 g of epichlorohydrin are added with stirring, and 61.31 g of a 47% KOH solution are subsequently slowly added dropwise. The metering rate here is selected so that the temperature of the reaction solution does not rise above 32° C. Towards the end of the addition, the batch becomes noticeably cloudy, with the viscosity increasing. When the addition is complete, the mixture is stirred at 70° C. for a further 15 h. The batch is cooled to room temperature, adjusted to pH 7 using dil. HCl, the organic phase is separated off and distilled in vacuo. Yield 86%, 195 g. Purity 98% (GC).

Example 9

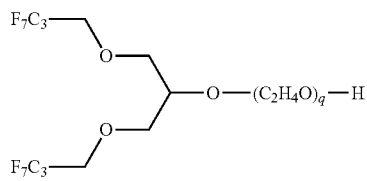

The alcohol prepared in Example 8 is reacted with ethylene oxide in a pressure reactor at 140° C. and a maximum pressure of 4 bar to give the corresponding fluorosurfactant. Different chain lengths can be achieved corresponding to the reaction time.

Three materials having a statistically distributed recurring unit of 8, 12 and 17 are obtained. The material is freed from low-boiling impurities by vacuum distillation. The static surface tension of the compounds and the CMC are reproduced in FIG. 1 as measurement values B9-8EO, B9-12EO and B9-17EO.

Determination of the Static Surface Tension

The static surface tensions γ of aqueous surfactant solutions having various concentrations c (grams per liter) are determined.

Instrument: Dataphysics tensiometer (model DCAT 11)

Temperature of the measurement solutions: 20°±0.2° C.

Measurement method employed: measurement of the surface tension using the Wilhelmy plate method in accordance with DIN EN 14370.

Plate: platinum, length=19.9 mm

In the plate method, the surface or interfacial tension of the surfactant solution is calculated from the force acting on the wetted length of a plate, in accordance with the following formula:

$$\gamma = \frac{F}{L \cdot \cos\theta} = \frac{F}{L}$$

γ=interfacial or surface tension; F=force acting on the balance; L=wetted length (19.9 mm); θ=contact angle.

The plate consists of roughened platinum and is thus optimally wetted so that the contact angle θ is close to 0°. The term cos θ therefore approximately reaches the value 1, so that only the measured force and the length of the plate have to be taken into account.

BRIEF DESCRIPTION OF FIGURES

FIG. 1 shows a comparison of the static surface tensions and CMCs of the synthesised short-chain fluorosurfactants with commercially available C6 (Capstone™) and C8 (Zonyl™) samples. Measurement values (denoted by *) above the bars are the CMCs determined in g/l. In the case of B7-12EO and B7-17EO, no CMC could be determined.

It can be seen from FIG. 1 that, in particular, the materials from Examples 2 and 9 cause a very good reduction in surface tension. Compared with commercially available C6 compounds, these materials in some cases do better and thus achieve the technical properties of C8 fluorosurfactants, which have been banned in the meantime.

The invention claimed is:

1. A compound of formula (I)

$$Rf-A-O-CH_2$$
$$\phantom{Rf-A-O-}\diagdown$$
$$\phantom{Rf-A-O-CH}RC-B-((CR^1R^2)_o(CR^3R^4)_pO)_q-X \quad (I)$$
$$\phantom{Rf-A-O-}\diagup$$
$$Rf'-A'-O-CH_2$$

where
- R is equal to H, alkyl, —OH or —CH$_2$—O-A"-Rf",
- Rf, Rf' and Rf" are each, independently of one another, equal to CF$_3$—CF$_2$—CF$_2$—O—CF(CF$_3$)—CH$_2$— or CF$_3$—(CF$_2$)$_n$—(CH$_2$)$_m$—,
- n is equal to 1-2,
- m is equal to 1,
- R$^1$-R$^4$ are each, independently of one another, equal to hydrogen or a C1-C4 alkyl group,
- o and p are each, independently of one another, 0-4, wherein o+p≥2, q≥1,
- A, A' and A" are each, independently of one another, equal to (O—(CR$^5$R$^6$)$_r$—(CR$^7$R$^8$)$_s$)$_t$,
- R$^5$-R$^8$ are each, independently of one another, equal to hydrogen or a C1-C4 alkyl group,
- r and s are each, independently of one another, 0-4,
- t is equal to 0 or 1,
- B is equal to (CH$_2$)$_{0-1}$—O or (CH$_2$)$_{0-1}$—NR',
- R' is equal to H or linear or branched alkyl, and
- X is equal to H or linear or branched alkyl.

2. The compound according to claim 1, wherein
- R is equal to H or —OH,
- B is equal to O, CH$_2$—O or CH$_2$—NR',
- R' is equal to H or CH$_3$,
- o and p are equal to 1-4,
- q is 1-100,
- ((CR$^1$R$^2$)$_o$(CR$^3$R$^4$)$_p$O)$_q$ is equal to polyethylene glycol, polypropylene glycol, polyisobutylene glycol, and/or polybutylene glycol units,
- t is equal to 0 or A, A' and A" are equal to —O—CH$_2$—CHR",
- R" is equal to H or CH$_3$, and
- X is equal to H or CH$_3$.

3. The compound according to claim 1, wherein Rf, Rf' and Rf" are identical and/or A, A' and A" are identical.

4. The compound according to claim 1, wherein
- Rf and Rf' are each, independently, equal to CF$_3$—CF$_2$—CF$_2$—O—CF(CF$_3$)—CH$_2$—, C$_2$F$_5$—CH$_2$— or C$_3$F$_7$—CH$_2$—,
- R is equal to H or —OH,
- B is equal to O or CH$_2$—NR',
- R' is equal to H or CH$_3$,
- ((CR$^1$R$^2$)$_o$(CR$^3$R$^4$)$_p$O)$_q$ is equal to a polyethylene glycol or polypropylene glycol unit,
- q is equal to 1-40,
- t is equal to 0, and
- X is equal to H.

5. The compound according to claim 1, wherein said compound is of formula (I'), $$Rf-O-CH_2$$
$$\phantom{Rf-O-}\diagdown$$
$$\phantom{Rf-O-CH}RC-B-((CR^1R^2)_o(CR^3R^4)_pO)_q-X. \quad (I')$$
$$\phantom{Rf-O-}\diagup$$
$$Rf'-O-CH_2$$

6. The compound according to claim 1, wherein said compound is of formulae (II), (IIIa), (IIIb), (IVa) or (IVb), $$Rf-O-\!\!\diagdown$$
$$\phantom{Rf-O-}HC-O-(C_2H_4O)_q-H \quad (II)$$
$$Rf'-O-\!\!\diagup$$

$$Rf-O-\!\!\diagdown$$
$$\phantom{Rf-O-}HOC-CH_2O-(C_2H_4O)_q-H \quad (IIIa)$$
$$Rf'-O-\!\!\diagup$$

$$Rf-O-\!\!\diagdown$$
$$\phantom{Rf-O-}HOC-CH_2O-(C_2H_4O)_q-CH_3 \quad (IIIb)$$
$$Rf'-O-\!\!\diagup$$

$$Rf-O-\!\!\diagdown$$
$$\phantom{Rf-O-}HOC-CH_2NH-(C_2H_4O)_q-H \quad (IVa)$$
$$Rf'-O-\!\!\diagup$$

$$Rf-O-\!\!\diagdown$$
$$\phantom{Rf-O-}HOC-CH_2NH-(C_2H_4O)_q-CH_3. \quad (IVb)$$
$$Rf'-O-\!\!\diagup$$

7. The compound according to claim 1, wherein said compound is of formulae (IIa) to (IId), (IIIa-1) or (IVa-1), $$CF_3CF_2CF_2OCF(CF_3)CH_2-O-\!\!\diagdown$$
$$\phantom{xxxxxxxxxxxxxxxxxxxxxx}HC-O-(C_2H_4O)_q-H \quad (IIa)$$
$$CF_3CF_2CF_2OCF(CF_3)CH_2-O-\!\!\diagup$$

$$CF_3(CF_2)_nCH_2-O-\!\!\diagdown$$
$$\phantom{xxxxxxxxxxxxxx}HC-O-(C_2H_4O)_q-H \quad (IIb)$$
$$CF_3(CF_2)_nCH_2-O-\!\!\diagup$$

$$CF_3CF_2CH_2-O-\!\!\diagdown$$
$$\phantom{xxxxxxxxxxx}HC-O-(C_2H_4O)_q-H \quad (IIc)$$
$$CF_3CF_2CH_2-O-\!\!\diagup$$

$$CF_3CF_2CF_2CH_2-O-\!\!\diagdown$$
$$\phantom{xxxxxxxxxxxxxx}HC-O-(C_2H_4O)_q-H \quad (IId)$$
$$CF_3CF_2CF_2CH_2-O-\!\!\diagup$$

$$CF_3CF_2CF_2OCF(CF_3)CH_2-O-\!\!\diagdown$$
$$\phantom{xxxxxxxxxxxxxxxxxxxxxx}HOC-CH_2O-(C_2H_4O)_q-H \quad (IIIa-1)$$
$$CF_3CF_2CF_2OCF(CF_3)CH_2-O-\!\!\diagup$$

$$CF_3CF_2CF_2OCF(CF_3)CH_2-O-\!\!\diagdown$$
$$\phantom{xxxxxxxxxxxxxxxxxxxxxx}HOC-CH_2NH-(C_2H_4O)_q-H. \quad (IVa-1)$$
$$CF_3CF_2CF_2OCF(CF_3)CH_2-O-\!\!\diagup$$

8. The compound according to claim 1, wherein said compound is selected from the following formulae:

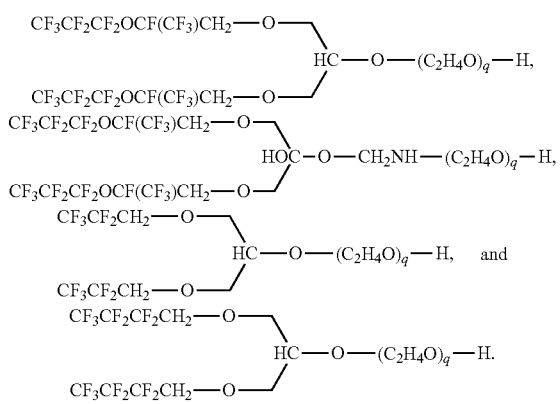

9. A paint, coating, printing ink, protective coating, special coating in electronic or optical applications, photoresist, top antireflective coating or bottom antireflective coating, developer solution and washing solution and photoresist for photolithographic processes, cosmetic product, agrochemical, floor polish, photographic coating or coating of optical elements comprising the compound according to claim 1 as an additive.

10. A composition comprising the compound according to claim 1 and a vehicle, and optionally further specific active substances.

11. The composition according to claim 10, wherein said composition is a paint or coating preparation, a fire-extinguishing composition, a lubricant, a washing composition or detergent, a de-icer composition, a developer solution for a photolithographic process, a washing solution for a photolithographic process, a photoresist composition for a photolithographic process, a cosmetic product, an agrochemical, a floor polish, or a hydrophobicizing composition for textile finishing or glass treatment.

12. A process for preparing the compound according to claim 1, said process comprising:
 a) converting an alcohol of formula (Va) or formula (Vb), which may optionally also be chain-extended,

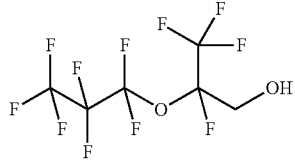
(Va)

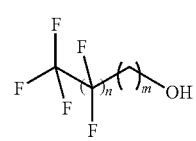
(Vb)

into a compound of formula (VI)

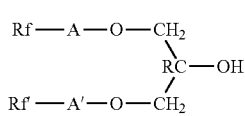
(VI)

where
R is equal to H, alkyl, —OH or —CH$_2$—O-A″-Rf″,
Rf, Rf' and Rf″ are each, independently of one another, equal to CF$_3$—CF$_2$—CF$_2$—O—CF(CF$_3$)—CH$_2$— or CF$_3$—(CF$_2$)$_n$—(CH$_2$)$_m$,
n is equal to 1-2,
m is equal to 1,
A, A' and A″ are each, independently of one another, equal to (O—(CR$^5$R$^6$)$_r$—(CR$^7$R$^8$)$_s$)$_t$,
R$^5$-R$^8$ are each, independently of one another, equal to hydrogen or a C1-C4 alkyl group,
r and s, independently of one another, are each 0-4, and
t is equal to 0 or 1, and
 b) polymerizing the compound of formula (VI) with an alkylene oxide.

13. A process for preparing the compound according to claim 5 where Rf'=Rf, said process comprising:
 a) reacting an alcohol of formula (Va) or formula (Vb),

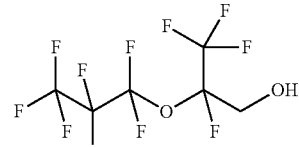
(Va)

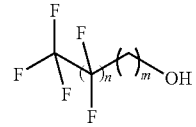
(Vb)

with 1,3-dichloropropan-2-ol or epichlorohydrin to give a compound of formula (VI'),

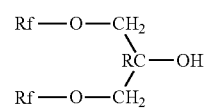
(VI')

where
R is equal to H,
Rf is equal to CF$_3$—CF$_2$—CF$_2$—O—CF(CF$_3$)—CH$_2$— or CF$_3$—(CF$_2$)$_n$—(CH$_2$)$_m$,
n is equal to 1-2, and
m is equal to 1, and
 b) polymerizing the compound of formula (VI') with an alkylene oxide.

14. A process for preparing the compound according to claim 1, said process comprising:
 a) converting an alcohol of formula (Va) or formula (Vb), which may optionally also be chain-extended,

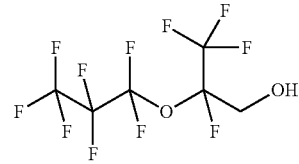
(Va)

-continued

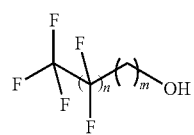
(Vb)

into a compound of formula (VII),

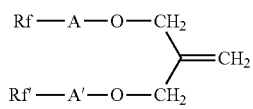
(VII)

where
Rf and Rf' are each, independently of one another, equal to $CF_3-CF_2-CF_2-O-CF(CF_3)-CH_2-$ or $CF_3-(CF_2)_n-(CH_2)_m$,
n is equal to 1-2,
m is equal to 1,
A or A' are each, independently of one another, equal to $(O-(CR^5R^6)_r-(CR^7R^8)_s)_t$,
$R^5$-$R^8$ are each, independently of one another, equal to hydrogen or a C1-C4 alkyl group,
r and s are each, independently of one another, 0-4, and
t is equal to 0 or 1,
b) epoxidizing the compound of formula (VII), and
c) reacting the epoxidized compound from b) with a polyethylene glycol or an aminopolyethylene glycol.

15. A process for preparing the compound according to claim 5 where Rf'=Rf, said process comprising:
a) reacting an alcohol of formula (Va) or formula (Vb),

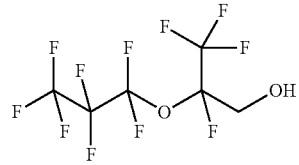
(Va)

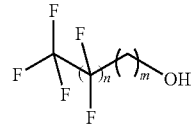
(Vb)

with 3-chloro-2-chloromethyl-1-propene to give a compound of formula (VII'),

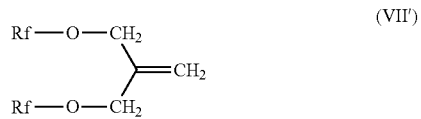
(VII')

where
Rf is equal to $CF_3-CF_2-CF_2-O-CF(CF_3)-CH_2-$ or $CF_3-(CF_2)_n-(CH_2)_m$,
n is equal to 1-2; and
m is equal to 1,
b) epoxidizing the compound of formula (VII'), and
c) reacting the epoxidized compound from b) with a polyethylene glycol or an aminopolyethylene glycol.

\* \* \* \* \*